United States Patent
Tedesco et al.

(10) Patent No.: US 10,261,020 B2
(45) Date of Patent: Apr. 16, 2019

(54) COST-EFFECTIVE RAMAN PROBE ASSEMBLY FOR SINGLE-USE BIOREACTOR VESSELS

(71) Applicant: Kaiser Optical Systems Inc., Ann Arbor, MI (US)

(72) Inventors: James M. Tedesco, Livonia, MI (US); Joseph B. Slater, Dexter, MI (US)

(73) Assignee: Kaiser Optical Systems Inc., Ann Arbor, MI (US)

( * ) Notice: Subject to any disclaimer, the term of this patent is extended or adjusted under 35 U.S.C. 154(b) by 0 days.

(21) Appl. No.: 15/398,096

(22) Filed: Jan. 4, 2017

(65) Prior Publication Data

US 2018/0188180 A1 Jul. 5, 2018

(51) Int. Cl.

| | |
|---|---|
| *G01N 21/65* | (2006.01) |
| *G01N 21/03* | (2006.01) |
| *G01J 3/02* | (2006.01) |
| *C12M 1/00* | (2006.01) |
| *C12M 1/34* | (2006.01) |
| *G01J 3/44* | (2006.01) |
| *G01N 21/85* | (2006.01) |

(52) U.S. Cl.
CPC ............ *G01N 21/65* (2013.01); *C12M 23/14* (2013.01); *C12M 41/00* (2013.01); *G01J 3/0208* (2013.01); *G01J 3/0291* (2013.01); *G01J 3/44* (2013.01); *G01N 21/0303* (2013.01); *G01N 21/8507* (2013.01); *G01N 2021/0321* (2013.01); *G01N 2021/651* (2013.01)

(58) Field of Classification Search
CPC ............... G01N 21/65; G01N 21/0303; G01N 2021/0321; G01N 2021/65; G01N 2021/0346; G01N 2021/656; G01N 2021/651; G01N 21/03; G01N 2021/6484; G01J 3/0218; G01J 3/0291; G01J 3/0237; G01J 3/0289; B01L 2300/0654; B01L 3/502715
See application file for complete search history.

(56) References Cited

U.S. PATENT DOCUMENTS

| | | | | |
|---|---|---|---|---|
| 3,531,211 | A * | 9/1970 | Staunton | ............ G01N 21/0303 250/573 |
| 5,037,199 | A * | 8/1991 | Hlousek | ............... G01N 21/255 356/246 |

(Continued)

*Primary Examiner* — Mohamed K Amara
(74) *Attorney, Agent, or Firm* — John G. Posa; Belzer PC

(57) ABSTRACT

Systems and methods are used to couple an optical sampling probe to a port in a single-use bioreactor bag for in-process monitoring. A combination of re-useable and disposable components maintain precision while reducing costs. A disposable barb with an integral window, received by the port of the reaction vessel, is coupled to a re-useable optic component with a focusing lens. A separate focus alignment tool is used to set the lens position to a precise focal point before placement of the optic component into the barb. The fixture includes a window to simulate the window in a barb component, a target with a known spectral signature, and a probe head coupled to a spectral analyzer. The axial position of the lens is adjusted with respect to the spacer component to maximize the spectral signature from a sample target, whereupon the spacer component is bonded to the lens mount.

20 Claims, 4 Drawing Sheets

(56) References Cited

U.S. PATENT DOCUMENTS

| | | | | |
|---|---|---|---|---|
| 5,112,127 A * | 5/1992 | Carrabba | G01J 3/44 | 250/227.23 |
| 5,181,082 A * | 1/1993 | Jeannotte | G01N 21/83 | 250/576 |
| 5,194,913 A * | 3/1993 | Myrick | G01N 21/65 | 250/458.1 |
| 5,381,237 A * | 1/1995 | Sela | G01N 21/255 | 250/458.1 |
| 5,404,218 A * | 4/1995 | Nave | G01N 21/65 | 356/246 |
| 5,999,255 A * | 12/1999 | Dupee | G01J 3/02 | 356/301 |
| 6,015,479 A * | 1/2000 | Boss | G01N 27/305 | 204/412 |
| 6,018,389 A * | 1/2000 | Kyle | G01J 3/02 | 356/301 |
| 6,028,666 A * | 2/2000 | Boss | G01J 3/02 | 356/301 |
| 6,333,784 B1 * | 12/2001 | Blasi | G01J 3/44 | 356/301 |
| 6,388,750 B1 * | 5/2002 | Liu | G01F 23/292 | 356/246 |
| 6,488,892 B1 * | 12/2002 | Burton | B01L 9/523 | 356/244 |
| 6,494,613 B2 * | 12/2002 | Terentiev | B01F 7/0005 | 366/279 |
| 6,542,231 B1 * | 4/2003 | Garrett | G01N 21/05 | 250/227.11 |
| 7,218,810 B2 * | 5/2007 | Hillendahl | G01N 21/253 | 356/246 |
| 7,379,783 B2 * | 5/2008 | Popp | G05B 23/0224 | 700/110 |
| 7,392,107 B2 * | 6/2008 | Popp | G05B 23/0224 | 700/109 |
| 7,701,571 B2 * | 4/2010 | Azimi | G01J 3/02 | 356/301 |
| 7,824,902 B2 * | 11/2010 | Selker | C12M 23/14 | 250/461.2 |
| 8,008,065 B2 * | 8/2011 | Selker | C12M 23/00 | 435/287.1 |
| 8,107,069 B2 * | 1/2012 | Wang | G01J 3/02 | 356/301 |
| 8,550,439 B2 * | 10/2013 | Terentiev | B01F 3/04248 | 261/121.1 |
| 8,817,259 B2 * | 8/2014 | Schick | G01N 21/0303 | 356/442 |
| 9,404,072 B2 * | 8/2016 | Koerperick | C12Q 1/02 | |
| 9,488,582 B2 * | 11/2016 | Sinfield | G01N 21/65 | |
| 9,568,418 B1 * | 2/2017 | Hug | G01J 3/10 | |
| 2003/0207331 A1 * | 11/2003 | Wilson, Jr. | B01J 19/0046 | 435/7.1 |
| 2004/0038390 A1 * | 2/2004 | Boege | B01L 7/52 | 435/288.7 |
| 2004/0077075 A1 * | 4/2004 | Jensen | B01L 3/5027 | 435/297.2 |
| 2005/0140973 A1 * | 6/2005 | Owen | G01J 3/44 | 356/301 |
| 2005/0265905 A1 * | 12/2005 | Young | B01J 19/0046 | 422/129 |
| 2006/0139632 A1 * | 6/2006 | Gerner | G01N 21/05 | 356/246 |
| 2006/0199260 A1 * | 9/2006 | Zhang | B01F 13/0059 | 435/293.1 |
| 2007/0002319 A1 * | 1/2007 | Knopp | G01J 3/02 | 356/301 |
| 2007/0231223 A1 * | 10/2007 | Young | B01J 19/0046 | 422/187 |
| 2010/0214562 A1 * | 8/2010 | Mahadevan-Jansen | A61B 5/0059 | 356/301 |
| 2015/0037445 A1 * | 2/2015 | Murphy | B29C 64/386 | 425/131.1 |
| 2015/0345689 A1 * | 12/2015 | Selker | F16L 58/185 | 435/289.1 |
| 2015/0346102 A1 * | 12/2015 | Chimenti | G01N 21/65 | 356/301 |
| 2015/0377701 A1 * | 12/2015 | Pawluczyk | G01J 3/0243 | 356/301 |
| 2015/0377787 A1 * | 12/2015 | Zeng | G01N 21/64 | 356/301 |
| 2016/0202124 A1 * | 7/2016 | Lambert | G01J 3/44 | 356/301 |
| 2016/0299060 A1 * | 10/2016 | Hokanson | G01N 21/31 | |
| 2017/0097297 A1 * | 4/2017 | Schick | G01N 21/0303 | |
| 2017/0224220 A1 * | 8/2017 | Tunnell | A61B 5/0071 | |

\* cited by examiner

COST-EFFECTIVE RAMAN PROBE ASSEMBLY FOR SINGLE-USE BIOREACTOR VESSELS

FIELD OF THE INVENTION

This invention relates generally to Raman spectroscopy and bioreactors and, in particular, to a Raman probe assembly for single-use bioreactor vessels.

BACKGROUND OF THE INVENTION

Single-use, disposable bioreactor vessels use a bag as opposed to a more expensive reusable culture vessel. The bag itself is typically made of a flexible plastic, but may be encased in a structure such as a rocker or a cuboid, or cylindrical steel support depending upon the experiment or reaction process under analysis. Commercial, single-use bioreactors have been available for over a decade and are now available from several manufacturers. Such bags commonly include one or more "ports" enabling the contents of the bag to be sampled and monitored.

Raman spectroscopy has become a powerful tool for use in conjunction with in situ process analysis. Sophisticated fiber-optic coupled Raman probes are now routinely used for process sampling in various industries, including bioreactor applications. It would be highly advantageous to couple a Raman probe to a bioreactor bag, through an available port, for example, but a tradeoff exists between the expense and complexity of the probe versus the bag assembly, which is designed to be disposable. Certainly the Raman probe itself cannot be disposable. Nonetheless, if certain components of the probe are not precisely aligned within the port, the required accuracy, repeatability, and reaction model transferability between reaction batches and probes will not be achieved.

There have been attempts to provide for disposable couplings to bioreactor vessel ports, but these attempts do not facilitate precise Raman sampling. U.S. Pat. No. 8,008,065 for example, discloses a port and sensor assembly adapted for use with an optical fiber-based phase fluorometric or Raman measurement system. A fiber or fiber bundle used as the excitation light source is anchored into a disposable insert shell through a ferrule or other suitable retention system. The diverging light from the fiber or fiber bundle is preferably collimated using a lens or lens system so that the collimated light is incident on a fluorescent dye spot. The fluorophore absorbs the excitation light and emits a fluorescent signal that impinges upon a collection system which is focused returned to a photo-diode through the same lens and fiber or fiber bundle. The fluorescent dye spot and fiber are mounted in a disposable shell that is inserted into a port affixed to the disposable bioreactor's lining.

While the system just described provides for a limited degree of fluorescence detection, it does not accommodate the exacting focusing requirements demanded of a state-of-the-art Raman sampling probe. Efficient and repeatable Raman sampling in a variably turbid sample medium, such as a bioreaction, requires the probe to be focused at a very short depth into the turbid sample from a disposable port window. Too deep a focus can negatively impact both the strength and the shape of the measured Raman spectrum.

SUMMARY OF THE INVENTION

This invention is directed to systems and methods for coupling a Raman probe to a port in a bioreactor vessel containing a reaction medium. The invention is applicable single-use bioreactor vessels in the form of flexible bags containing cell-culture and/or other biological media in liquid form. Such single-use bags are commonly provided with a hollow, tubular port adapted for attachment to various forms of instrumentation. In accordance with the instant invention, a Raman or other focusing probe head is coupled to the port for in-process monitoring.

A point of novelty resides in a unique combination of re-useable and disposable components to maintain precision while reducing costs. The solution made possible by the invention uses a fairly high-precision-thickness window sealed into a relatively inexpensive disposable barb that is inserted into the port of the reaction vessel. The barb is coupled to an optic component, which contains one or more expensive focusing lenses. To accurately locate the focus of the lens assembly at a precise, predetermined depth outside the window in the reaction medium, inventive end-optic hardware and assembly/alignment tooling are used.

The barb component has a distal end including an integral window with proximal and distal surfaces. The barb component is physically configured to be received by the port in a bioreactor vessel such that the distal surface of the window is exposed to the reaction medium. The system further includes an optic component configured to be received by the barb component. The optic component includes a proximal end adapted for coupling to a Raman probe head, and a distal end including a lens for focusing light to, and collecting light from, a sample focus in the reaction medium for analysis by a Raman analyzer coupled to the probe head. In preferred embodiments, the predetermined distance is on the order of 0.005+/−0.001", though the invention is not limited in this regard.

Apparatus for setting the focus of the lens at the predetermined distance may include an adjustable spacer component disposed between the lens and the window. More particularly, the lens is retained within a lens mount axially moveable within the optic component and, once the predetermined distance is established, the proximal end of the spacer component is bonded to the lens mount with the distal end of the spacer in intimate contact with the proximal surface of the window. A spring in the hollow optic component may be used to bias the lens mount distally to ensure that the distal end of the spacer component maintains contact with the proximal surface of the window, thereby ensuring that the lens maintains a precise relationship to the window.

A separate fixture is preferably used as a focus alignment tool to set the lens at a precise position before placement of the optic component into the barb. The tool includes a simulation window to simulate the window in a barb component, a target with a known Raman spectral signature and a Raman probe head coupled to a Raman analyzer. One or more precision shims are used to position the target at the predetermined distance from the distal surface of the simulation window. With the distal end of the spacer component against the simulation window, the axial position of the lens in the lens mount is adjusted with respect to the spacer component to maximize the Raman spectral signature from the sample, whereupon the spacer component is bonded to the lens mount. Conveniently, the target may be a silicon wafer, which has a strong Raman peak that is maximized when positioned at the focal point of the probe.

Methods of coupling an optical sampling probe head to a port into a bioreactor vessel containing a reaction medium are also disclosed and described.

DETAILED DESCRIPTION OF THE PREFERRED EMBODIMENTS

This invention enables a sophisticated Raman sampling probe to be used with disposable/single-use bioreactor vessels/bags by providing a trade-off in terms of those components that may be retained, and those components that are disposable. This is accomplished at low cost, and without a compromise in terms of sampling accuracy and effectiveness.

The preferred embodiments provide for a multi-part system including a disposable barb assembly with an integrated and sealed window operative to pass wavelengths of interest. The disposable assembly, which is received at one end by a conventional reactor bag port, connects at the other end to a Raman probe. A sanitary clamp between the barb assembly and the probe enables the expensive probe components to be re-used. To ensure that the focusing optic integrated into the disposable barb assembly has the required accuracy, the invention includes a focus assembly tool and associated method to simulate the production assembly to place the focus of the lens at the ideal depth in the sample region opposite the window.

Figure 1A:
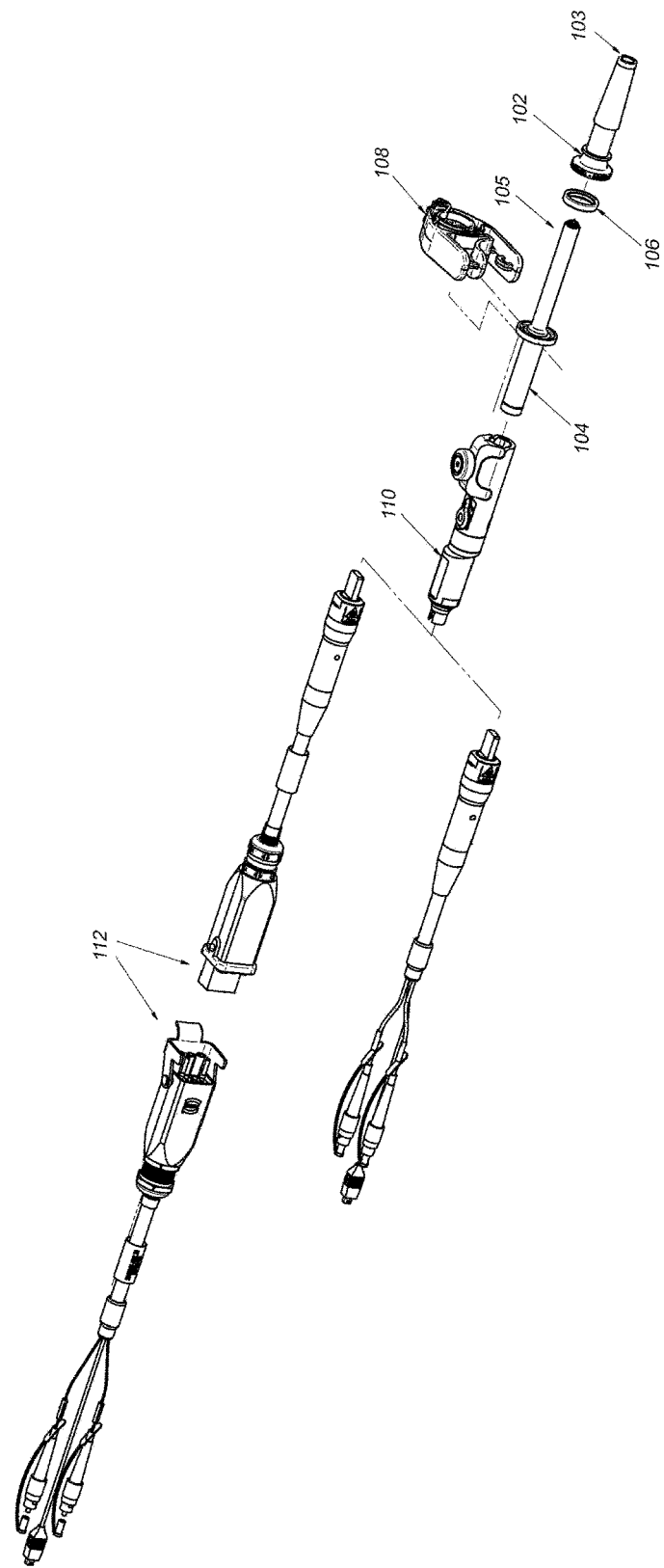
FIG. 1A is an exploded view.
Figure 1B:
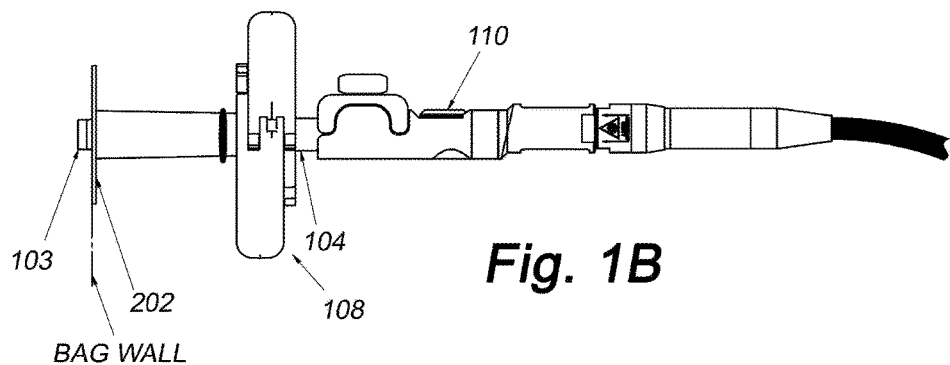
FIG. 1B is an assembled view.
Figure 2A:
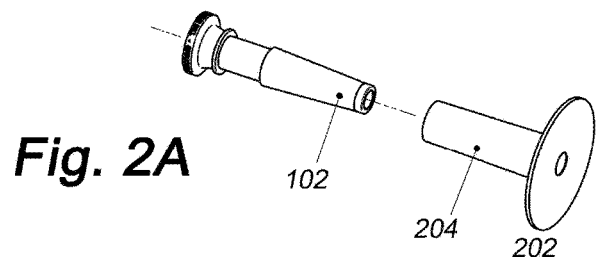
FIG. 2A shows a barb component prior to insertion into a bioreactor port.
Figure 2B:
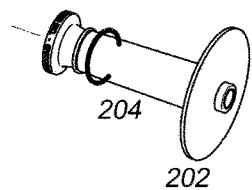
FIG. 2B shows a barb component received within a bioreactor port such that the window of the barb is exposed to the contents of the reaction vessel.
Figure 2C:
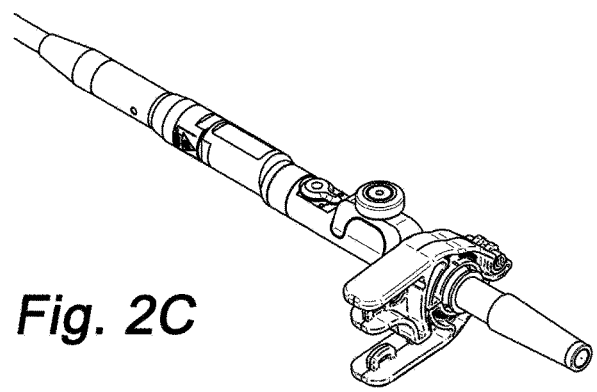
FIG. 2C is an oblique assembled view but not coupled to a bioreactor port.

FIG. 1A is an exploded view of the overall arrangement. FIG. 1B shows an assembled system. Disposable barb fitting 102 couples to a port 202 shown in FIGS. 2A, 2B. The barb fitting 102 is a tube with dimensions that enable the fitting to contact a tube stop 204 of port 202 so as to provide a liquid-tight seal. As shown in FIG. 2B, a "zip-tie" 205 may be used for back-up retention. The distal end of the barb fitting includes an integrated window 103 (FIG. 1A) as described in more detail below. The proximal end of the barb fitting 102 is configured to receive end optic component 104. A sanitary fitting seal 106 and clamp 108 provide for a liquid-tight engagement between the end optic 104 and barb fitting 102. The distal end 105 of the end optic 104 includes a focusing lens described below in conjunction with a preferred alignment technique.

The proximal end of end optic 104 is coupled to a probe head component 110, which, in turn couples to one or more different optical fiber assemblies 112, 113. Component 110, which may comprise the MR Probe available from Kaiser Optical Systems, Ann Arbor, Mich., includes filters, beam splitters and optics to receive laser excitation from one fiber and deliver a Raman signal to a spectrograph by way of a collection fiber. As described in issued U.S. Pat. No. 6,907, 149, the entire content of which is incorporated herein by reference, the MR Probe head generates collimated, coaxial images of the excitation and collection fibers for focusing onto or into a variety of sample scenarios using a variety of different end optics. Further details of the MR probe may be found at http://www.kosi.com/na_en/products/raman-spectroscopy/raman-probes-sampling/mr-probe-head.php with the understanding that this invention is not limited in terms of the probe head used. Indeed, the invention is readily applicable to any focusing optical probe, including fluorescence probes, such that as used herein "Raman" should be taken to include these other sampling modalities.

Port 202 is in fact integral to the disposable bioreactor bag, such that the window of the inserted barb is immersed into the liquid contents of the bag, thereby enabling Raman monitoring of the liquid. When the reaction is complete, the end optic component 104 is un-clamped and removed from the barb 102. The entire bag/port/barb pieces may then be safely disposed of—such pieces cannot be reused as they have been in contact with, and contaminated by, the bioreaction materials. The optic component 104, however, can be re-used, as it has not been similarly contaminated.

An important point of novelty of this invention is to relegate the precision and expense in the re-useable components, while minimizing the cost of the disposable components. Toward this end, a challenge is setting the focus of the assembled system to be at a very precise depth outside the window in the reaction medium. A representative focus depth in typical applications might be 0.005"+/−0.001". Maintaining this precision is necessary to maximize sensitivity and consistency of results from batch to batch and from probe to probe. Even if all of the focal depth tolerance were accommodated by the window thickness, this would still require more precise and more costly window thickness specifications. This is undesirable since, by definition, the window must be disposable, as it comes in contact with the reaction.

The solution made possible by this invention is to use a fairly high-precision-thickness window sealed into a fairly simple disposable barb. While the barb may be machined from stainless steel, for example, in the preferred embodiments the barb is constructed from an injection-moldable material using a process that is certified for bio applications. A remaining challenge, however, is to interface the barb to the optic component 104, which contains the focusing lens, in such a way as to accurately put the focus at the desired depth outside the window. This is accomplished using inventive design of the end optic hardware, disposable barb, and assembly/alignment tooling.

Figure 3A:
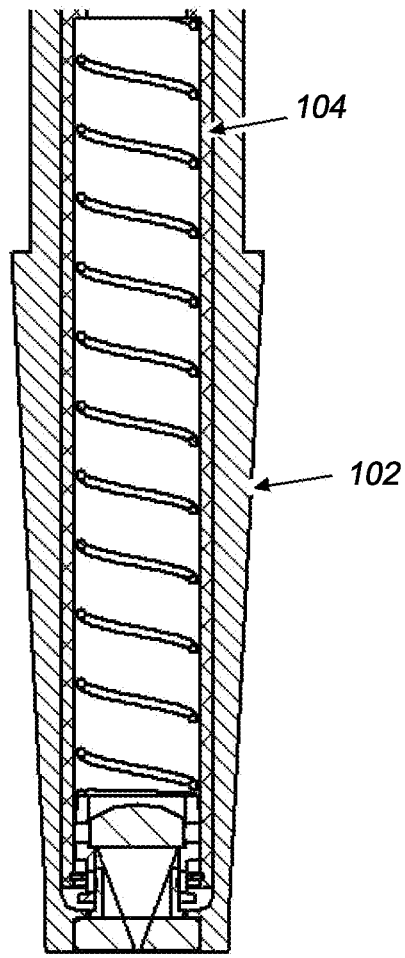
FIG. 3A is a cross section depicting an optic component within a barb with a spring-biased lens mount.
Figure 3B:
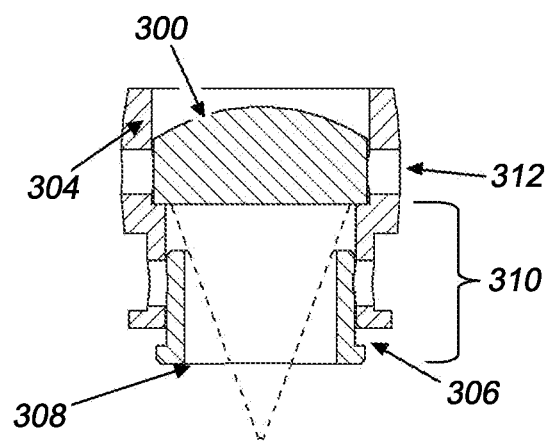
FIG. 3B is a detail drawings of a lens in a lens mount bonded to a spacer component.

FIG. 3B shows a focus lens subassembly, and FIG. 3A shows how the focus lens subassembly is spring-loaded into the optic component 104 received within the barb 102. As shown in FIG. 3B, the focus lens subassembly includes a component 302 that supports the focusing lens 300. Component 302 may include a curvature at 304 to accommodate variations in machining assembly, and to facilitate free axial movement of the sub-optic assembly in the optic component 104. A distal spacer component 306 is slidingly received with the proximal component 302. The distal-most end surface of the spacer component 306 makes contact with the surface of the window in the barb, and it is distance 310 that is varied to precisely set the focal depth of the probe with respect to a disposable barb/window assembly as described in further detail below.

Figure 4:
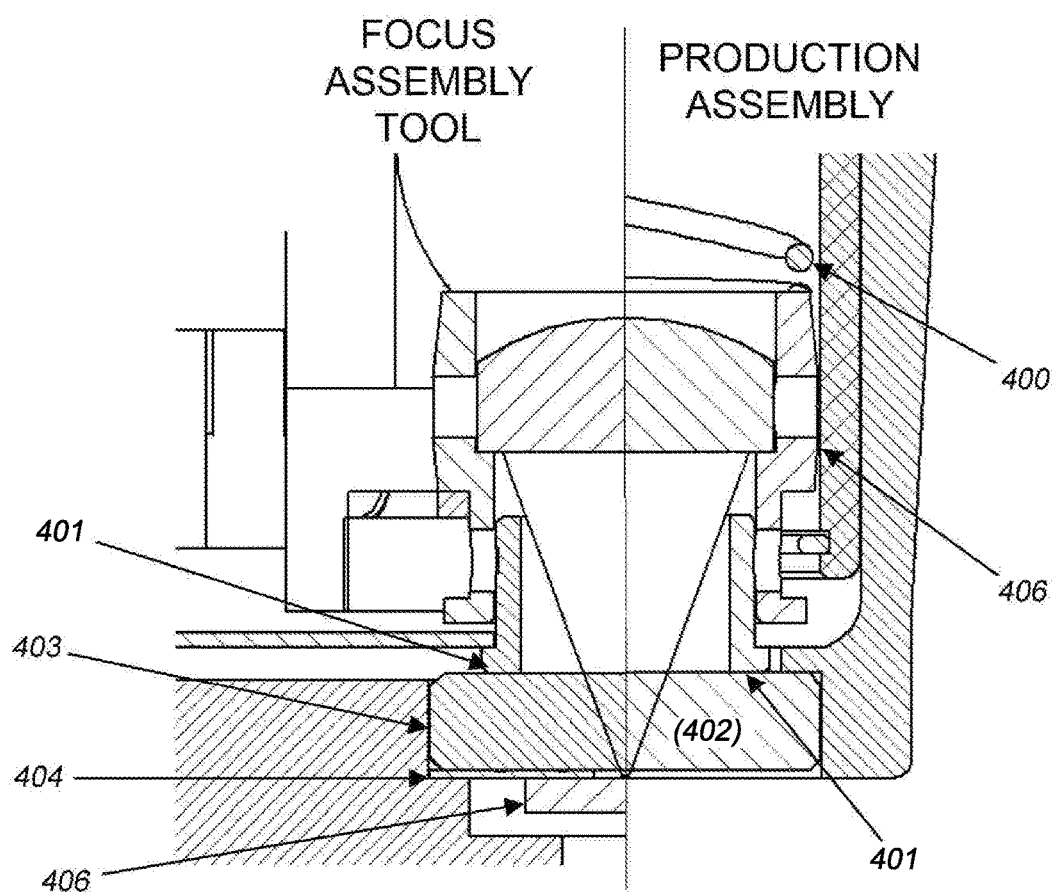
FIG. 4 illustrates a focus assembly tool on the left and a production assembly on the right.

The focus-setting tool is intended to optically simulate the end-use Raman sampling environment as used with a disposable bioreactor bag. FIG. 4 is a drawing that shows the focus lens sub assembly in a focus tool on the left side of the illustration, and in a production setting on the right side. When positioned in the tool, the focus lens 300 is optically aligned into a mount that, when inserted into the barb, comes into direct mechanical spring-loaded contact with the inner surface of the barb window 402. The alignment tooling loads the mount against an identical precision-thickness window 402'. Precision shims 404 are used to locate a flat silicon wafer 406 at the target focal depth outside the window, at a predetermined or desired distance of 0.005", for example.

A Raman probe head (not shown), is pre-aligned to collimate and combine the Raman excitation and collection fiber paths (i.e., a standard MR Raman probe head available from Kaiser Optical Systems, Inc.) is located at the same nominal distance from the window as in the final product installation. This distance is not critical, as it is in a nominally collimated space.

During setup using the tool, the probe head is connected to a Raman analyzer, the focus lens is bonded into its mount 302, and the spacer component 306 is loaded against the window at reference 401. The axial position of the mounted focus lens is adjusted with respect to spacer 306 to a position that maximizes the Raman signal of the silicon wafer. The focus lens mount 302 and spacer 306 are then bonded in that position with a UV-cure adhesive.

The right side of FIG. 4 shows the corresponding production assembly following shim placement and signal optimization. The spring 400 ensures that the lens assembly remains in contact with the actual window 402 in the barb component 102. The curvature at 406 provides clearance for self-aligning of the optical components. As such, when this lens/mount assembly is mated with any collimated probe head, and loaded against any disposable barb window of sufficiently similar thickness, an accurate and repeatable focal depth is achieved.

The invention claimed is:

1. A system for coupling a Raman probe head to a port in a bioreactor vessel containing a reaction medium, the system comprising: a barb component with a distal end including an integral window with proximal and distal surfaces, the barb component being physically configured to be received by the port into the bioreactor vessel such that the distal surface of the integral window is exposed to the reaction medium in the bioreactor vessel; an optic component configured to be received by the barb component, the optic component including a proximal end adapted for coupling to a Raman probe head and a distal end including at least one lens for focusing light to, and collecting light from, a sample focus in the reaction medium for analysis by a Raman analyzer coupled to the Raman probe head; and wherein the at least one lens in the optic component and the integral window in the barb component are optically aligned along a common optical axis, and the at least one lens in the optic component is moveable within the optic component along the common optical axis; and an adjustable spacer component used to move the at least one lens along the common optical axis so as to adjust the distance between the at least one lens in the optic component and the integral window in the barb component, such that the sample focus of the at least one lens is set at a precise, predetermined distance from the distal surface of the integral window in the reaction medium, the distance between the at least one lens and the integral window is fixed using the adjustable spacer component to maintain the sample focus at the predetermined distance.

2. The system of claim 1, wherein the barb component, including the integral window, is a disposable component.

3. The system of claim 1, wherein the at least one lens is operative to focus laser excitation light from the Raman probe head to the sample focus and collimate the light including Raman spectra collected from the sample focus, such that the optic component carries counter-propagating excitation and collection beams of light.

4. The system of claim 1, further including a focus alignment tool used to adjust and align the adjustable spacer component to ensure that the sample focus of the at least one lens is set at the precise, predetermined distance from the distal surface of the integral window.

5. The system of claim 4, wherein: the at least one lens is retained within a lens mount axially moveable within the optic component; the adjustable spacer component includes proximal and distal ends and, wherein the predetermined distance is established using the focus alignment tool, the proximal end of the adjustable spacer component is bonded to the lens mount with the distal end of the spacer adapted for contact with the proximal surface of the integral window; and further including a spring in the optic component for biasing the lens mount distally to ensure that the distal end of the adjustable spacer component maintains contact with the proximal surface of the integral window.

6. The system of claim 5, wherein: the focus alignment tool is configured to receive the lens mount including the at least one lens and the adjustable spacer component; and the focus alignment tool is used to adjust and bond the spacer component to the lens mount wherein the predetermined distance is established.

7. The system of claim 6, wherein the focus alignment tool further includes: a simulation window with proximal and distal surfaces to simulate the integral window in the barb component; a target with a known Raman spectral signature; one or more shims to position the target at the predetermined distance from the distal surface of the simulation window; an alignment Raman probe head coupled to an alignment Raman analyzer, the Raman probe head being optically aligned with the target through the simulation window and the at least one lens in the lens mount; and whereby, with the distal end of the adjustable spacer component positioned against the simulation window, the axial position of the at least one lens in the lens mount is adjusted with respect to the adjustable spacer component to maximize the Raman spectral signature from the sample, whereupon the adjustable spacer component is bonded to the lens mount.

8. The system of claim 7, wherein the target is a silicon wafer.

9. The system of claim 1, wherein the bioreactor vessel is a flexible, disposable bag.

10. The system of claim 1, wherein the reaction medium is a liquid.

11. A method of coupling a Raman probe head to a port into a bioreactor vessel containing a reaction medium, the method including the steps of: providing a barb component with a distal end including an integral window with a distal surface; inserting the barb component into the port of the bioreactor vessel such that the distal surface of the integral window is exposed to the reaction medium; providing an optic component including a proximal end and a distal end including a focusing lens in a lens mount that is axially moveable within the optic component; coupling the proximal end of the optic component to a Raman probe head that outputs laser excitation and collects Raman spectra in a counter-propagating beam of light; inserting the optic component into the barb component; and providing and adjusting a spacer component between the focusing lens in the optic component and the integral window in the barb component to focus the counter-propagating light at a precise, predetermined distance from the distal surface of the integral window in the reaction medium; and fixing the position of the focusing lens in the optic component with respect to the integral window in the barb component wherein the predetermined distance is established.

12. The method of claim 11, wherein the barb component, including the integral window, is a disposable component.

13. The method of claim 11, including the step of coupling the Raman probe head through optical fibers to a remote laser excitation source and Raman spectrograph for analysis of the collected spectra.

14. The method of claim 11, including the step of using a separate alignment tool to adjust the spacer component so as to set the focus of the focusing lens at the precise, predetermined distance from the distal surface of the integral window.

15. The system of claim 14, including the steps of: supporting the focusing lens in a lens mount axially moveable within the optic component; and fixing the proximal end of the spacer component to the lens mount with the distal end of the spacer component being in contact with the proximal surface of the integral window wherein the predetermined distance is established using the focus alignment tool.

16. The method of claim 15, including the step of spring-biasing the lens mount distally to ensure that the distal end of the spacer component maintains contact with the proximal surface of the integral window.

17. The method of claim 16, including the steps of: providing a focus alignment fixture for receiving the focusing lens in the lens mount with the spacer component; adjusting the spacer component in the fixture to establish the predetermined distance; and bonding the spacer component to the lens mount so that the predetermined distance is achieved.

18. The method of claim 17, wherein the focus alignment fixture further includes: a simulation window with proximal and distal surfaces to simulate the integral window in the barb component; a target with a known Raman spectral signature; one or more shims to position the target at the predetermined distance from the distal surface of the simulation window; an alignment Raman probe head coupled to an alignment Raman analyzer, the Raman probe head being optically aligned with the target through the simulation window and the focusing lens in the lens mount; and with the distal end of the spacer component positioned against the simulation window, adjusting the axial position of the focusing lens in the lens mount with respect to the spacer component to maximize the Raman spectral signature from the sample.

19. The method of claim 18, wherein the target is a silicon wafer.

20. The method of claim 19, wherein: the bioreactor vessel is a flexible, disposable bag; and the reaction medium is a liquid.

* * * * *